United States Patent
Wong et al.

(10) Patent No.: US 9,873,910 B1
(45) Date of Patent: Jan. 23, 2018

(54) METHOD OF USING TWO-STAGE NUCLEIC ACID REACTION AND DETECTION TUBE

(71) Applicant: Credo Biomedical Pte Ltd., Singapore (SG)

(72) Inventors: Jr Winston Wong, New Taipei (TW); Stephen Chang-Chi Kao, New Taipei (TW); Ying-Ta Lai, New Taipei (TW); Ming-Fa Chen, New Taipei (TW)

(73) Assignee: Credo Biomedical Pte Ltd., Singapore (SG)

( * ) Notice: Subject to any disclaimer, the term of this patent is extended or adjusted under 35 U.S.C. 154(b) by 0 days.

(21) Appl. No.: 15/730,757

(22) Filed: Oct. 12, 2017

Related U.S. Application Data

(63) Continuation of application No. 15/614,626, filed on Jun. 6, 2017, now Pat. No. 9,816,136.

(30) Foreign Application Priority Data

Sep. 21, 2016 (TW) .............................. 105130394 A
Sep. 21, 2016 (TW) .............................. 105214422 U

(51) Int. Cl.
| | | |
|---|---|---|
| *C12Q 1/68* | (2006.01) | |
| *C12P 19/34* | (2006.01) | |
| *B01L 7/00* | (2006.01) | |
| *B01L 3/00* | (2006.01) | |

(52) U.S. Cl.
CPC .............. *C12Q 1/686* (2013.01); *B01L 3/502* (2013.01); *B01L 7/52* (2013.01); *C12P 19/34* (2013.01); *C12Q 1/6844* (2013.01); *C12Q 1/6851* (2013.01); *C12Q 2537/149* (2013.01)

(58) Field of Classification Search
CPC .... C12Q 1/686; C12Q 1/6851; C12Q 1/6844; C12Q 2537/149; B01L 7/52; B01L 3/502; C12P 19/34
See application file for complete search history.

(56) References Cited

U.S. PATENT DOCUMENTS

| | | | |
|---|---|---|---|
| 3,661,265 A | 5/1972 | Greenspan | |
| 7,238,520 B2 * | 7/2007 | Brown | .................. B01L 3/5029 422/408 |

FOREIGN PATENT DOCUMENTS

| | | |
|---|---|---|
| EP | 0 073 551 A2 | 3/1983 |
| TW | 201423104 A | 6/2014 |

\* cited by examiner

*Primary Examiner* — Sally A Merkling
(74) *Attorney, Agent, or Firm* — Winston Hsu

(57) ABSTRACT

The present invention provides a method of using a two-stage nucleic acid reaction and detection tube. First, a reaction and detection tube is provided. Then a reaction is performed by using a liquid in the storing space of the second tube, following by putting the dipstick into the dipstick fixing space of the connector. The first tube, the second tube and the connector is assembled together, wherein the dipstick is placed both in the dipstick fixing space of the connector and the detection space of the first tube. The reaction and detection tube is rotated from bottom to top, thus making the liquid in the storing space of the second tube flow into the liquid collection space through the diversion unit and then contact the dipstick in the dipstick fixing space. A detection result is then observed from the dipstick.

20 Claims, 4 Drawing Sheets

METHOD OF USING TWO-STAGE NUCLEIC ACID REACTION AND DETECTION TUBE

CROSS REFERENCE TO RELATED APPLICATIONS

This application is a continuation application of application Ser. No. 15/614,626 filed on Jun. 6, 2017, and included herein by reference.

BACKGROUND OF THE INVENTION

1. Field of the Invention

The present invention relates to the field of biology, and more particularly, to a method of using a two-stage nucleic acid reaction and detection tube which is to perform polymerase chain reaction (PCR) and/or nucleic acid detection and can be directly processed in the same tube without any liquid transfer.

2. Description of the Prior Art

Polymerase chain reaction (hereinafter referred to as "PCR") is a technology for rapid amplification of DNA, and its principle and the main operational steps may include: (a) denature: using a relatively high temperature (90~95° C.) for the double-stranded DNA dissociating into single stranded DNA, which is then used as a template for replication; (b) primer annealing: when the temperature is lowered to a predetermined temperature, primers will be adhered to the correct positions of the target genes; (c) primer extension: the reaction temperature will be adjusted to 72° C., in combination of using magnesium ions as enzyme cofactors, the deoxy-ribonucleotide triphosphate (hereinafter referred to as "dNTPs") will be sequentially adhered to and after the primer by DNA polymerases, in accordance with the base sequence of nucleotides on the template, so as to form a synthetic DNA fragment. By repeating the three-step process of temperature oscillation, the number of the target gene can be doubled in each repetition of the three-step process, thus can be $10^9$ times after 40 cycles of the three-step process. The signal of the target gene can therefore be amplified. Accordingly, the PCR detection technology is generally used for detecting molecular signals in clinical diagnosis, such as pathogen diagnosis, diagnosis of genetic disease, diagnosis of cancer tumors, or the like. The RT-PCR technique which is derived from PCR also has similar principle and application, therefore is widely used in current techniques clinical diagnosis.

Devices used to perform PCR or RT-PCR reactions often include heat resistant plastics as the materials of the reaction tube. The amplification of nucleic acid is achieved by using the thermostat metal to repeatedly increase and decrease the temperature for the tube so as to reach different temperatures in each three-step process. In current system, the system with thermostat metal requires a relatively lager space, the entire temperature control system may occupy a larger space and heat capacity ratio. In addition, according to current practice of operation, one test required 30-35 cycles and the time required for the reaction is about two to three hours, consequently, most of the time of the process relies on waiting for the rise of the temperature or cooling metal, making it difficult to reduce the reaction time.

In addition, the amplification of the target gene in PCR or RT-PCR is often conformed by gel electrophoresis, which can separate the nucleic acid by its molecular size. After the PCR or PT-PCR process, the product containing amplified target gene (hereinafter "the product") is transferred from the tube into a previously prepared gel well and since the nucleic acid contains negatively charge in neutral or alkaline solution, it will move toward the anode wherein the moving speed is proportional to it molecular weight. By this process, it can be checked if the amplification of nucleic acid successes or not. However, even the gel electrophoresis detection exhibits high accuracy, it still takes several hours to complete the PCR/RT-PCR and gel electrophoresis. For those diagnoses which are willing to obtain results in short time, it would be not suitable to use PCR/PT-PCR to approach the diagnosis or inspection. In addition, when performing the gel electrophoresis, the product of PCR/RT-PCR needs to be transferred from the reaction vessel to the gel well, and the product is easily contaminated during transferring, which may result in false positive.

To shorten the reaction time, a technology that uses thermal convection for performing PCR has been developed (hereinafter "thermal convection PCR"). This technology was first designed by Krishnan et al., T and it uses a cylindrical tube of the Rayleigh-Benard cell with two different heating sources which are disposed at two corresponding sites of the tube. In general, the top level of the reagent is maintained at around a temperature of about 60° C., while the bottom temperature is about 95° C. By the temperature differences arising from the cylindrical cavity through the upper and lower end, it can drive the flow of fluid in the chamber, thus processing the PCR reaction. This embodiment may also be applied to RT-PCR. From this, other technology derived from it with similar principle has been developed for commercial use, such as the use of isolated single point of heating technology called "insulated isothermal polymerase chain reaction" (iiPCR), which performs the RCR reaction in a closed capillary in combination of three points heating sources; or by using non-contact irradiation heating source, which contains heating point of the cylindrical tube closed loop design to achieve the effect for the PCR or RT-PCR. By using the thermal convection process, PCR as well as RT-PCR will not need to use thermostat metal to be repeated temperature oscillation of three steps of the reaction temperature, so it can save a lot of repeated heating and cooling time, thus reducing the use of temperature control metal.

In order to avoid the product of the PCR/RT-PCR from being contamination, which would result in false positive, there are more and more detection technologies used to replace original gel electrophoresis, such as using a specific binding fluorescence chemical compound to combine the target gene. When a laser beam with appropriate wavelength is applied, the chemical compound will emit fluorescence, and it will be detected by the equipment. The intensity of the fluorescence is proportional to the amount of the product of PCR/RT-PCR, so the method can reach in-situ qualitative or even quantitative inspection, thus reducing the reaction temperature.

In another aspect, there is one common inspection technology that uses a specific binding dipstick for the target gene to detect the product of PCR/RT-PCR. The method includes using two different antigens that can specifically bind antibody, for example, the first type of antigen is DIG or TexasR, and the second type of antigen is Avidin or FITC. After the reaction, the product would contain these two types of antigens. In addition, one side of the dipstick is attached to an Ag gel, emulsion beads or other coloring compounds, which can specifically bind the antibodies of the above-mentioned antigens, such as Biotin-anti-FITC or other specific binding protein; the other side of the dipstick is attached to a cotton pad; and some portions of the dipstick is coated to the antibody of the first type of antigens such as anti-DIG, anti-TaxasR or other specific binding antibody. After the reaction, the product of PCR or RT-PCR is transferred to the end of the lipstick that contains the coloring compound, and the first type of antigen will specifically bind the first type of antibody to forma first type antigen-antibody-coloring complex. The complex will then move toward the terminal end with cotton pad. When it moves at the part containing the second type of antibody, the second type of antigen will specifically bind the second type of antibody and thus exhibit colors. The user can therefore obtain the result according to the colors. Since there are only several minutes that are used to complete the dipstick detection, it can save more time in comparison to convention electrophoresis method. In other situation, the antibody can be replaced by the nucleic acid probe depending on different requirement.

As described above, since the thermal convection PCR and the dipstick detection method can save a lot of time comparing to convention PCR/RT-PCR and gel electrophoresis method, it is widely used in the industry in this field. However, there is still not found a detection tube that can operate both thermal convection PCR and the dipstick detection method in single tube. Conventional method is to complete the thermal convection PCR in one tube and then to transfer the reagent onto the dipstick so as to carry out the entire detection method. However, since the product is difficult to take out from the tube, it is not such convenient to operate the system, and it also raises the risk of contamination.

Accordantly, there is still a need to have a two-stage detection tube that can both perform polymerase chain reaction (PCR) and/or nucleic acid dipstick detection and can be directly processed in the same tube without any liquid transfer.

SUMMARY OF THE INVENTION

To solve the abovementioned problem, the present invention is directed to a two-stage nucleic acid tube. By using said tube, no additional steps of transferring chemical reagents are required. After performing the convection PCR or PT-PCR, the first tube can directly connect the second tube with dipstick and the connector, the nucleic acid reaction can be performed in one single device and the result can be checked by the dipstick.

To achieve the above-mentioned object, according to one preferred embodiment of the present invention, the device includes a first tube including a first connection portion and a detection space. The detection space is used for placing a dipstick with one cotton end; a second tube including a second connection portion and a storing space, wherein the storing space is used to accumulate the sample of the target gene and corresponding reagents. The connector includes a first portion and a second portion, which respectively connects the first connection portion and the second connection portion, wherein the first portion of the connector comprises a diversion unit and a liquid collection space, the diversion unit can lead the liquid in the storing space to the liquid collection space, and the second portion comprises a dipstick fixing space for placing the dipstick, and the dipstick fixing space is connected to the liquid collection space.

After performing the thermal convection PCR and/or the RT-PCR, the dipstick can be placed in the first tube and the connector in advance, and the first tube, the second tube and the connector are assembled to forma closed detection tube. After assembling the three components, the assembled device can be rotated from bottom to top with about 180 degrees to make the reagents flow into the liquid collection space through the diversion unit of the connector and thus contact the dipstick in the dipstick fixing space. By using the capillary action by the dipstick with one end attaching cotton, the PCR product is delivered from one end with the dipstick coated with coloring material toward the other end of the cotton dipstick. In this manner, the antigen carried by the products can specifically combine the antibody which is coated on the test paper, so the detection result can be observed through the detection space. By the techniques set forth in the present invention, the object can be achieved by performing the convection PCR and/or RT-PCR to detect the products in one single device.

These and other objectives of the present invention will no doubt become obvious to those of ordinary skill in the art after reading the following detailed description of the preferred embodiment that is illustrated in the various figures and drawings.

DETAILED DESCRIPTION

The following context and drawings illustrate the principles of the present disclosure according to one preferred embodiment of the present invention. As used herein, directional terms as may be used such as "horizontal," "vertical," "proximal," "distal," "front", "rear", "left," "right," "inner," "outer," "interior" and "exterior" relate to an orientation of the disclosed mixing device from the perspective of a typical user, and do not specify permanent, intrinsic features or characteristics of the device.

Figure 1:
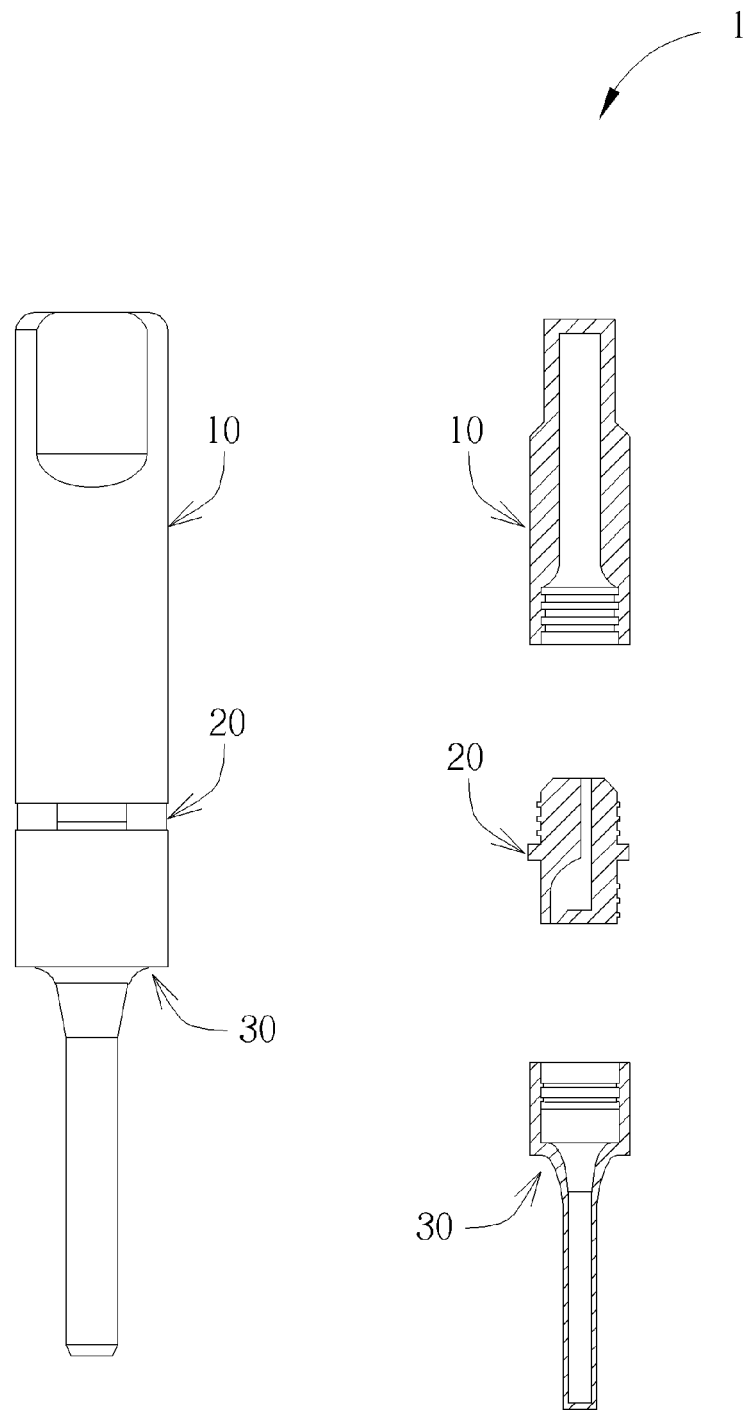
FIG. 1 shows an exploded drawing and assembly drawing of the detection tube according to one preferred embodiment of the present invention.
Figure 2A:
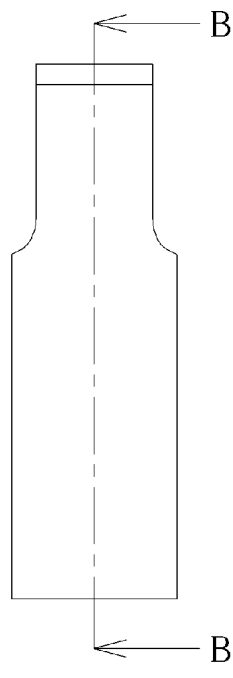
FIG. 2A is an outward appearance of the first tube from one side.
Figure 2B:
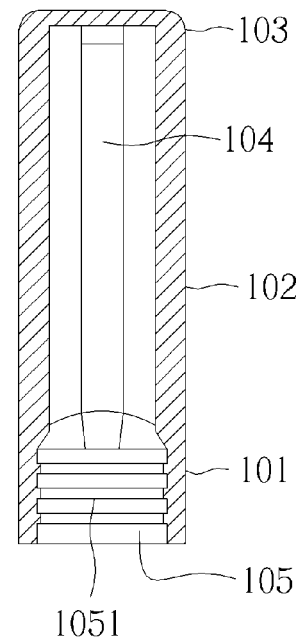
FIG. 2B is a cross-sectional view taken along line BB' in FIG. 2A.
Figure 3A:
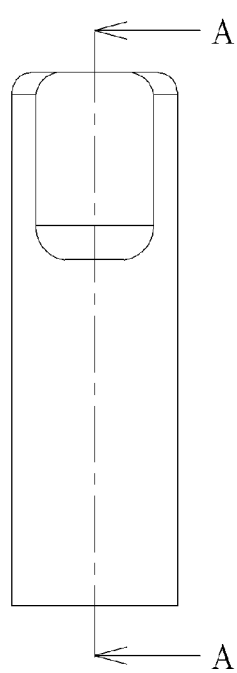
FIG. 3A is an outward appearance of the first tube from another side.
Figure 3B:
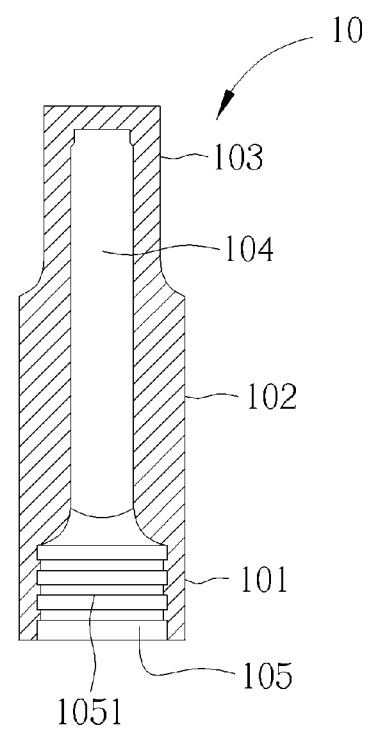
FIG. 3B is a cross-sectional view taken along line AA' in FIG. 3A.
Figure 4:
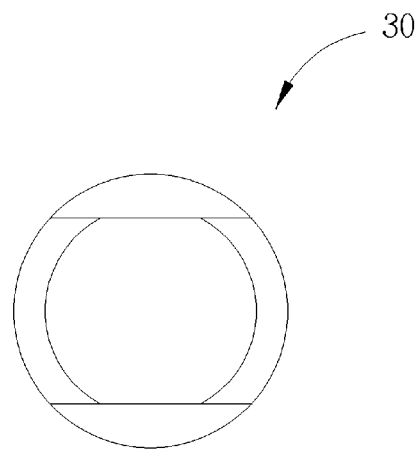
FIG. 4 is a bottom view of the first tube.

Please refer to FIG. 1. The reaction tube 1 in one preferred embodiment of the present invention includes a first tube 10, a second tube 30, and a connector 20 connecting the first tube 10 and the second tube 30.

Please refer to FIG. 1, FIG. 2A, FIG. 2B, FIG. 3A, FIG. 3B and FIG. 4. The first tube 10 in the previous embodiment is a transparency tube made of poly-carbonate, which comprises a first connection portion 101, a holding portion 103, an observation window 102 disposed between the first connection portion 101 and the holding portion 103, and an detection space 104. In the present embodiment, the outward appearance of the observation window 102 of the first tube 10 is a smooth and arced plane. The holding portion 103 is located at one end of the first tube 10, which has two corresponding surfaces to be clipped by the user's finger for observing the reaction result. At the other end corresponding to the holding portion 103, a first snap structure 105 is disposed in the inner side of the first tube 10. In the present application, the first snap structure 105 includes at least an annular projection unit 1051 for connecting the connector 20. The inner space of the first tube 10 is the detection space 104 which is used to accommodate a dipstick containing one cotton end. The detection space 104 has an oblong shape in its cross-section, so the detection space 104 contains a pair of parallel surfaces and a pair of curved surfaces. Thus, the outer surface of the first tube 10 and the inner surface walls of the first tube 10 together forms a flat convex lens. When the dipstick is placed in the detection space 104, the features shown on the dipstick can be enlarged and are easy to watch. Besides, when placing the dipstick, the end containing the cotton is positioned at the other side far from the first snap structure 105.

Figure 5A:
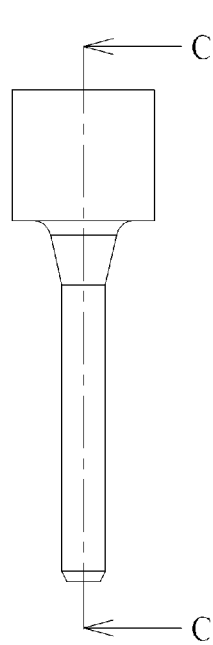
FIG. 5A is an outward appearance of the second tube.
Figure 5B:
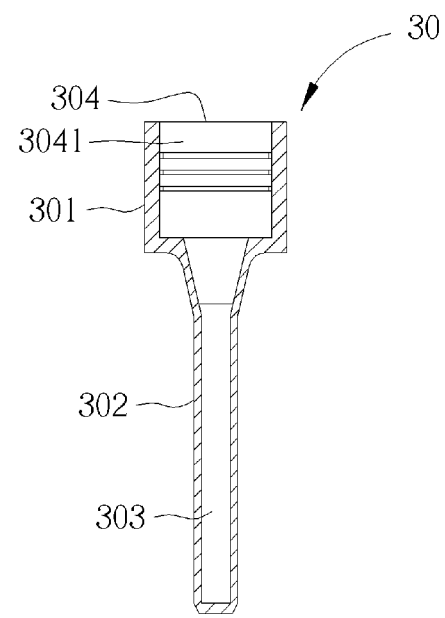
FIG. 5B is a cross-sectional view taken along line CC' in FIG. 5A.

Please refer to FIG. 1, FIG. 5A and FIG. 5B. The second tube 30 is a hollow transparent tube having a portion with a greater inside diameter for connection the connector 20 and a capillary portion with a smaller inside diameter. The second tube 30 has a second connection portion 301 which has similar structure with that of the first connection portion 101 of the first tube 10. A second snap structure 304 is formed inside the second tube 30 and contains at least an annular projection unit 3041 for connecting the connector 20. The storing space 303 inside second tube 20 can accumulate the reagents required in the reaction.

Figure 6A:
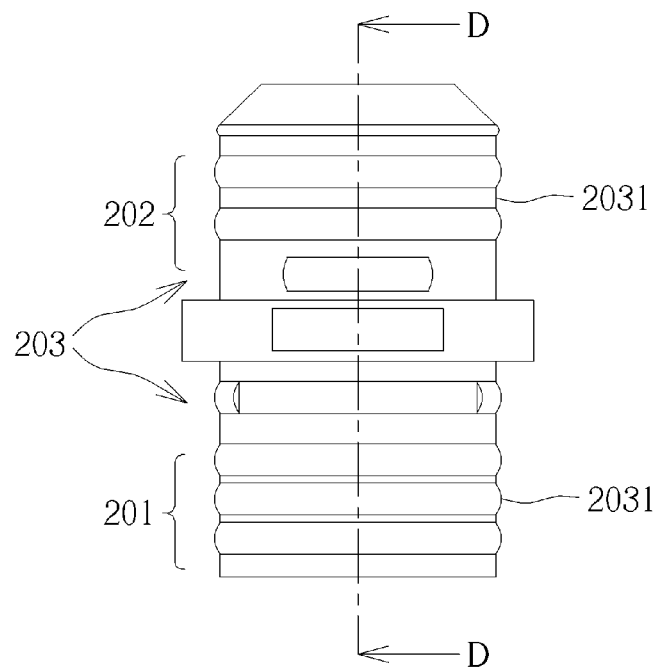
FIG. 6A is an outward appearance of the connector.
Figure 6B:
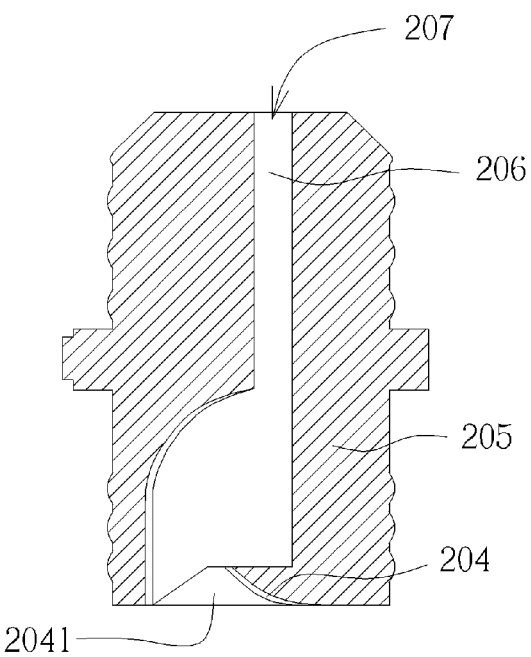
FIG. 6B is a cross-sectional view taken along line DD' in FIG. 6A.

As shown in FIG. 1, FIG. 6A and FIG. 6B, the connector 20 of the present embodiment is an elastomer preferably made of silica gel so the connector 20 has a hardness lower than the hardness of the first tube 10 and the second tube 30. The connector 20 has a first portion 201 and a second portion 202 to respectively connect the first connection portion 101 of the first tube 10 and the second connection portion 301 of the second tube 30. In detail, both the first portion 201 and the second portion 202 have a third snap structure 203 and in one preferred embodiment, the third snap structure 203 contains a plurality of annular projection units 2031. When assembling the first tube 10, the second tube 30 and the connector 20, the annular projection unit 1051 of the first tube 10 and the annular projection unit 3041 of the second tube 30 can make the connector 20 slightly deformed, forming a compact assembling between the annular projection units of the first portion 201 and the second portion 202, and the corresponding annular projection units 1051, 3041 of the first tube 10 and the second tube 30 so as to establish a tightly integrated sealing structure.

Please refer to FIG. 6B, the first portion 201 of the connector 20 includes a diversion unit 204 and a liquid collection space 205, and the second portion 202 includes a dipstick fixing space 206, which is a long channel with an uniform caliber. The dipstick fixing space 206 has an outlet 207 used as an entrance for putting the dipstick there through. The liquid collection space 205 has an inlet adjacent to the diversion unit 204 and an outlet adjacent to the dipstick fixing space 206, wherein the opening area of the outlet is greater than that of the inlet. By doing this, it can prevent inappropriate contact between the reagents and the dipstick and avoid the capillarity movement of the reagent toward the other side of the dipstick, which may result in unwanted reaction to the antibody coated on the dipstick. Further, it can also prevent the reagent flowing into the detection space 104 in the first tube 10, which causes wrong interpretation of the result.

In the present embodiment, the diversion unit 204 is a diversion slope 2041 inclining toward the liquid collection space 205. When the user converts the detection tube 1 with 180 degrees, for example, turns the detection tube in FIG. 1 upside down, the diversion slope 2041 can guide the liquid in the second tube 202 to the liquid collection space 205. Since the liquid collection space 205 is a hollow chamber for accumulating liquid and connected to the dipstick fixing space 206, when the liquid flows into the liquid collection space 205, the liquid would contact the dipstick and soon processes the PCR/RT-PCR detection reaction. Besides, as the inlet of the liquid collection space 205 (referred to the interface between the liquid collection space 205 and the diversion unit 204) is narrower than the outlet of the liquid collection space (referred to the interface between the liquid collection space 205 and the dipstick fixing space 206), the liquid can be guided along the predetermined direction. In increasing the reaction speed, the contact region of the liquid and dipstick is increased by forming the outlet of the liquid collection space 205 at the longer border of the dipstick fixing space 206. By doing this, when the liquid flows out from the liquid collection space 206, it can contact the dipstick with a bigger area, so the reaction speed can be increased.

When using the detection tube, the to-be-analyzed target gene, the specific binding antibody or other necessary are added into the second tube 30 and a thermal convection PCR/RT-PCR. Thereafter, the product of PCR/RT-PCR now contains the antigens called DIG or Avidin. Then, the dipstick that is coated by coloring material, specific binding antibody and absorbent cotton in its terminal ends is placed into the dipstick fixing space 206 of the connector 20, following by assembly the connector 20 and the second portion 301 of the second tube 30 together to make the dipstick fix in the storing space 303 of the second tube 30. In the present embodiment, the coloring material is gold (Au) gel, the specific binding antigen is DIG in which the corresponding antibody is Anti-DIG, the other specific binding antigen is Avidin in which its corresponding antibody is Biotin, and Biotin can bind Ag gel to form an Ag gel-Biotin complex.

After the thermal convection PCR/RT-PCR, there is no need to remove the reagent in the second tube 30, instead, the connector 20, the first tube 10 and the second tube 30 are assembled according to the structure in FIG. 1 thereby forming a completely compact detection tube 1. Thereafter, the detection tube 1 is turned 180 degrees, that is, making the structure if FIG. 1 upside down, so the reagents of the thermal convection PCR/RT-PCR originally in the second tube would flow into liquid collection space 205 and the dipstick fixing space 206 via the guide slope 204 as to contact the dipstick in the dipstick fixing space 206. Since there is a cotton pad at one terminal end of the dipstick, the reagents of the PCR/RT-PCR will gradually move to the terminal containing the cotton because of the capillary action. When the movement of the reagent is processing, Avidin will specifically combine Biotin to form Avidin-Biotin-Ag gel complex, which will further move to the place with Anti-DIG coating. Thus, it will combine with DIG and give color signals for detection. Consequently, the coloring can show the result of detection.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of using a two-stage nucleic acid reaction and detection tube, comprising:
    providing a reaction and detection tube, comprising:
        a first tube, comprising a first connection portion and a detection space;
        a second tube, comprising a second connection portion and a storing space; and
        a connector, comprising a first portion and a second portion, wherein the first portion of the connector comprises a diversion unit and a liquid collection space, and the second portion comprises a dipstick fixing space, which connects the liquid collection space;
    performing a reaction by using a liquid in the storing space of the second tube;
    putting the dipstick into the dipstick fixing space of the connector;
    assembling the first tube, the second tube and the connector together by connecting the second portion of the connector to the second connect portion of the second tube and by connecting the first portion of the connector to the first connection portion of the first tube, thereby forming the closed reaction and detection tube, wherein the dipstick is placed both in the dipstick fixing space of the connector and the detection space of the first tube; and
    rotating the reaction and detection tube from bottom to top, thus making the liquid in the storing space of the second tube flow into the liquid collection space through the diversion unit and then contact the dipstick in the dipstick fixing space; and
    observing a detection result from the dipstick.

2. The method of using the two-stage nucleic acid reaction and detection tube according to claim 1, wherein the reaction is a thermal convection PCR or a thermal convection RT-PCR.

3. The method of using the two-stage nucleic acid reaction and detection tube according to claim 1, wherein liquid comprises a target gene and antigens.

4. The method of using the two-stage nucleic acid reaction and detection tube according to claim 3, wherein the antigens comprise digoxigenin (DIG) or avidin.

5. The method of using the two-stage nucleic acid reaction and detection tube according to claim 1, wherein the dipstick is coated by a coloring material and antibodies.

6. The method of using the two-stage nucleic acid reaction and detection tube according to claim 5, wherein the coloring material is gold (Au).

7. The method of using the two-stage nucleic acid reaction and detection tube according to claim 5, wherein the antibodies comprise anti-digoxigenin (anti-DIG) or biotin.

8. The method of using the two-stage nucleic acid reaction and detection tube according to claim 5, wherein the dipstick further comprises a cotton at one end in the detection space of the first tube.

9. The method of using the two-stage nucleic acid reaction and detection tube according to claim 8, after rotating the reaction and detection tube, the target gene is delivered along dipstick toward the end with the cotton by capillary action.

10. The method of using the two-stage nucleic acid reaction and detection tube according to claim 1, wherein the detection result is observed from an observation window showing the dipstick.

11. The method of using the two-stage nucleic acid reaction and detection tube according to claim 1, wherein an out peripheral contour of the first tube is a round tube and the detection space is an oblong space having two corresponding planar surfaces.

12. The method of using the two-stage nucleic acid reaction and detection tube according to claim 1, wherein the second tube further comprises a capillary portion for placing the liquid.

13. The method of using the two-stage nucleic acid reaction and detection tube according to claim 1, wherein the dipstick fixing space of the connector is an elongated channel with a uniform diameter.

14. The method of using the two-stage nucleic acid reaction and detection tube according to claim 13, wherein the liquid collection space comprises an outlet for leading the liquid, and the outlet is disposed at a longer side of the dipstick fixing space.

15. The method of using the two-stage nucleic acid reaction and detection tube according to claim 1, wherein the liquid collection space is a chamber connecting the dipstick fixing space.

16. The method of using the two-stage nucleic acid reaction and detection tube according to claim 1, wherein the liquid collection space has an inlet adjacent to the diversion unit and an outlet adjacent to the dipstick fixing space, wherein the opening area of the outlet is greater than that of the inlet.

17. The method of using the two-stage nucleic acid reaction and detection tube according to claim 1, wherein the diversion unit is a guide slope inclining toward the liquid collection space for leading the liquid in the second tube toward the liquid collection space.

18. The method of using the two-stage nucleic acid reaction and detection tube according to claim 1, wherein the first connection portion comprises a first snap structure and the second connection portion comprises a second snap structure for connecting the connector.

19. The method of using the two-stage nucleic acid reaction and detection tube according to claim 18, wherein the first snap structure or the second snap structure comprises an annular projection unit for connecting the connector.

20. The method of using the two-stage nucleic acid reaction and detection tube according to claim 1, wherein a hardness of the connector is less than a hardness of the first tube and a hardness of the second.

* * * * *